United States Patent [19]

Keyes et al.

[11] Patent Number: 4,591,557

[45] Date of Patent: May 27, 1986

[54] PROCESS AND MATERIALS FOR PRODUCING SOLUBLE BIOLOGICAL MEDIATORS FROM WHITE BLOOD CELLS

[75] Inventors: Lynne D. Keyes, New Brunswick; Douglas Testa, Neshanic Station, both of N.J.

[73] Assignee: Interferon Sciences, Inc., New Brunswick, N.J.

[21] Appl. No.: 446,160

[22] Filed: Dec. 2, 1982

[51] Int. Cl.[4] .................. C12P 21/00; A01N 1/02; C12P 21/02; C12P 19/34; C12N 5/00; C12N 5/02; C01G 9/00

[52] U.S. Cl. .................................. 435/68; 435/2; 435/70; 435/91; 435/240; 435/241; 435/811; 424/101

[58] Field of Search ............... 435/68, 70, 2, 240, 435/241, 811; 424/101

[56] References Cited

U.S. PATENT DOCUMENTS

| 4,376,821 | 3/1983 | Braude | 435/68 |
| 4,376,822 | 3/1983 | Braude | 435/68 |
| 4,382,027 | 5/1983 | Braude | 424/85 |
| 4,440,675 | 4/1984 | Braude | 435/811 |

FOREIGN PATENT DOCUMENTS

0063482 10/1982 European Pat. Off. .
81/03498 12/1981 PCT Int'l Appl. .

OTHER PUBLICATIONS

Brawerman, "The Isolation of Messenger RNA from Mammalian Cells", Methods in Enzymology 30F:605 (1974).

Johnson, R. A. et al., "Augmentation of Phytohaemagglutinin Mitogenic Activity by RBS Membranes," Fed. Proc. 29: 370, 1970.

Yachnin, S., et al., Proceedings of the Fourth Annual Leucocyte Culture Conference, pp. 37–47, Jun. 1969.

Chang, T. W., et al., Journal of Immunology, vol. 128, Feb. 1982, pp. 585–589.

Georgiades, J. A., et al., Interferon: Properties and Clinical Uses, 1980, pp. 97–110.

Wheelock, E. F., National Cancer Institute Monograph 22, 1965, pp. 73–76.

Wheelock, E. F., Science, vol. 149, 1965, pp. 310–311.

Barkhan, P. and Ballas, A., Nature, vol. 200, (Oct. 12, 1963), pp. 141–142.

Epstein, L. B., Biology of the Lymphokines (ed. Cohen, S.), Academic Press, New York, 1979, pp. 458–459.

Hall, L. S. and Gordon, D. S., Journal of Immunological Methods, vol. 12 (1976), pp. 31–38.

Johnson, R. A., et al., Cellular Immunology, vol. 3, pp. 186–197 (1972).

Kenyon, R. H., et al., Infection and Immunity, (Dec., 1977), vol. 18, No. 3, pp. 840–846.

Kishimoto, R. A., et al., Infection and Immunity, (Jan., 1978), vol. 19, No. 1, pp. 194–198.

Kornfeld, S., et al., Proc. N.A.S., (1969), vol. 63, pp. 1439–1446.

Kornfeld, R., et al., The Jorunal of Biological Chemistry, vol. 215, No. 10, May 25, 1970, pp. 2536–2545.

Maddison, S. E., et al., Infection and Immunity, (Jul., 1979), vol. 25, No. 1, pp. 237–248.

Maddison, S. E., et al., The American Journal of Tropical Medicine and Hygiene, vol. 28, No. 6, Nov. 1979, pp. 955–961.

(List continued on next page.)

Primary Examiner—Thomas G. Wiseman
Assistant Examiner—James Martinell
Attorney, Agent, or Firm—Vincent P. Pirri

[57] ABSTRACT

A process and cellular system for producing soluble biological mediators, including cytokines, lymphokines, monokines and interferons, and mRNA therefor, from white blood cells is provided. The process involves treating white blood cells with a mitogenic or antigenic agent in the presence of a controlled amount of red blood cells. Increases in production of the soluble biological mediator, gamma interferon, on the order of 5 to 10 fold have been achieved by maintaining the ratio of red blood cells to white blood cells between 10 to 1 and about 50 to 1. The process is particularly useful in producing HuIFN-γ with PHA-P.

8 Claims, 2 Drawing Figures

OTHER PUBLICATIONS

Michalowski, A., *Third Annual Leucocyte Culture Conference*, pp. 41–52.

Ruscetti, F. W., et al., *The Journal of Immunology*, (May, 1975), vol. 114, No. 5, pp. 1513–1517.

Tarnvik, A., *Acta Path. Microbiol. Scand. Section B*, vol. 78, pp. 733–740 (1970).

Tarnvik, A., *Acta Path. Microbiol. Scand. Section B*, vol. 79, pp. 635–640 (1971).

Tarnvik, A., *Acta Path. Microbiol. Scand. Section B*, vol. 79, pp. 588–594 (1971).

Tarnvik, A., et al., *Acta Path. Microbiol. Scand. Section B*, vol. 80, pp. 107–114 (1972).

Todd, C. W., et al., *Transactions of the Royal Society of Tropical Medicine and Hygiene*, (1981), vol. 75, No. 6, pp. 783–787.

Wallen, W. C., et al., *Cellular Immunology*, (1973), vol. 6, pp. 110–122.

Webb, P. J., et al., *Cellular Immunology*, (1980), vol. 52, pp. 370–380.

FIG. 1

PROCESS AND MATERIALS FOR PRODUCING
SOLUBLE BIOLOGICAL MEDIATORS FROM
WHITE BLOOD CELLS

BACKGROUND OF THE INVENTION

1. Field Of The Invention

This invention relates to a process and materials for producing soluble biological mediators, including cytokines, lymphokines, monokines and interferons, from white blood cells. it also relates to the production of messenger RNA (mRNA) for such substances from white blood cells. More specifically, the invention relates to enhancing the ability of mitogenic and antigenic agents to induce the production of soluble biological mediators. The invention is particularly useful in producing human gamma interferon (HuIFN-$\gamma$), also known as immune interferon or Type II interferon, and mRNA therefor.

2. Description of the Prior Art

As known in the art, mitogenic agents, i.e., substances that induce mitosis and cell transformation, and antigenic agents can be used to stimulate white blood cells to produce soluble biological mediators. See, for example, J. A. Georgiades, et al, "Human Immune Interferon: Purification And Activity Against a Transformed Human Cell", in *Inteferon: Properties And Clinical Uses*, (Khan et al, eds.), Wadley Institutes of Molecular Medicine, Dallas, Tex. 1980, pages 97–110. In particular, since as early as 1965, it has been known that the mitogen, phytohemagglutinin (PHA), an extract of red kidney beans, can be used to stimulate the production of HuIFN-$\gamma$ in leukocyte suspensions. See E. F. Wheelock "Inhibition of Virus Induced Leukemia In Mice By A Non-Tumor Virus", *National Cancer Institute Monograph* 22, 1965, pages 73–76; E. F. Wheelock, *Science*, Vol. 149, 1965, pages 310–311.

Production of soluble biological mediators in general and gamma interferon in particular from white blood cells has been notoriously difficult because of the small yields obtained by prior art methods A common element of these prior art methods has been the removal from the white blood cell population of essentially all red blood cells. This removal has typically been accomplished by one of two methods. In the more common method, ammonium chloride (NH$_4$Cl) has been used to lyse the red blood cells commingled with the white blood cells. See J. A. Georgiades, et al, supra. Alternatively, centrifugation in Ficoll-Hypaque gradients has been used to fractionate and thus separate the white blood cells from the red blood cells.

In direct contrast to these prior art methods, as discussed in detail below, it has been found unexpectedly that the production of soluble biological mediators and mRNA therefor can be significantly increased by the incorporation of a controlled amount of red blood cells with the white blood cells. Specifically, increases in the production of human gamma interferon on the order of 5 to 10 fold have been achieved by maintaining the ratio of red blood cells to white blood cells above about 10 to 1.

SUMMARY OF THE INVENTION

In view of the low production of soluble biological mediators and mRNA therefor by prior art methods using white blood cells, it is an object of the present invention to increase the production of such substances by white blood cells. In particular, it is an object of the invention to enhance the production of soluble biological mediators and mRNA therefor induced in white blood cells by mitogenic and antigenic agents. A further object of the invention is to provide an easy-to-use method for obtaining a mixture of red and white blood cells having a red blood cell to white blood cell ratio within defined limits.

In accordance with certain aspects of the invention, a process for producing a soluble biological mediator or mRNA therefor from white blood cells is provided which comprises inducing production of the soluble biological mediator or mRNA therefor by treating white blood cells with a mitogenic or antigenic agent in the presence of an effective amount of red blood cells or a red blood cell fraction which includes cell membranes so as to enhance the induction of the soluble biological mediator or mRNA therefor by the mitogenic or antigenic agent by a factor of about two or more in comparison with the amount of mediator or mRNA produced in the absence of red blood cells. The red blood cells can be added to either purified white blood cell populations or white blood cell populations containing red blood cells in order to adjust the content of red blood cells to enhance the effect of the mitogenic or antigenic agent or the red blood cell/white blood cell combination can be achieved in the process of purifying the white blood cells.

In accordance with a further aspect of the invention a cellular system for use with a mitogenic or antigenic agent is provided which comprises a mixture of white blood cells and an effective amount of red blood cells or a red blood cell fraction which includes cell membranes sufficient to enhance the inductive effect of the mitogenic or antigenic agent on the white blood cells by a factor of about two or more in comparison with the inductive effect in the absence of red blood cells.

In accordance with an additional aspect of the invention a process for producing a mixture of white blood cells and red blood cells for use with a mitogenic or antigenic agent is provided which comprises the steps of:

centrifuging a buffy coat which contains white and red blood cells;

removing a first white cell layer which contains some red blood cells from the centrifuged product so formed;

diluting said first white cell layer with a liquid compatible with both white and red blood cells;

centrifuging the diluted first white cell layer; and removing a second white cell layer containing some red blood cells from the centrifuged product so formed.

In connection with certain preferred embodiments, the processes and materials of the invention are applied to the production of gamma interferon and mRNA therefor, and in particular to the production of human gamma interferon and mRNA therefor.

The attainment of the above objects of the invention as well as other objects is described below in connection with the description of the preferred embodiments.

DESCRIPTION OF THE PREFERRED EMBODIMENTS

As discussed above, the present invention relates to a process and materials for enhancing the induction of cytokines, lymphokines, monokines and interferons, collectively referred to herein as soluble biological mediators, from white blood cells by mitogenic and antigenic agents.

By way of illustration, Tables 1 and 2 present lists of various soluble biological mediators and mitogenic and antigenic agents to which the invention relates. It is to be understood that these lists are not to be construed as limiting the invention in anyway, and, in particular, the invention is applicable to biological response modifiers and mitogenic and antigenic agents not currently known in the art, as well as to substances currently known but not specifically enumerated in Tables 1 and 2.

Also, with regard to Table 2, it should be noted that some of the mitogenic and antigenic agents in this Table are the product of the action of other agents listed in the Table. For example, interleukin 1 and interleukin 2, which also appear in Table 1 and which are induced by, among other things, phytohemagglutinin (PHA), are themselves mitogens. The invention is also to be construed as applicable to mitogenic and antigenic agents of this type.

TABLE 1
SOLUBLE BIOLOGICAL MEDIATORS

| | |
|---|---|
| AEF | Allogeneic effect factor |
| AgDMIF | Antigen dependent macrophage inhibiting factor |
| AIM | Antibody inhibiting material |
| ANP | Anti-neoplaston A |
| ASS | Antigen specific enhancer (of the T-cell dependent antibody response) |
| ASTCF | Antigen specific T-cell factor |
| BAF | B-cell activating factor |
| BCF | Basophil chemotactic factor |
| BF | Blastogenic factor |
| CHA | Chemotactic factor |
| CSA | Stimulating activities |
| CRP | C reactive protein |
| DBMCF | Differentiating B memory cell factor |
| DDHF | Desensitization of delayed hypersensitivity factor |
| DLF | Differentiating lymphocyte factor |
| DMMF | Depressor of monocyte migration |
| ECHF | Eosinophil chemotactic factor |
| FIF | Feedback inhibition factor |
| GAF | Glucocorticord antagonizing factor |
| GRF | Genetically restricted factor |
| HFIgE | Helper factor for IgE |
| HRF | Histamine releasing factor |
| IA | Inflamatory activity factor |
| IDS | Inhibitor of DNA synthesis |
| IF | Interferon complex |
| IFEF | Interferon enhancing factor |
| IFN-γ | Gamma Interferon |
| IgESF | IgE suppressor factor |
| IIFIF | Immune interferon inhibitory factor |
| IRA | Immunoregulatory globulin |
| ISF | Immunosuppressive factor from mastorytoma |
| IVPF | Increasing vascular permeability factor |
| LAF | Interleukin 1 |
| LAF | Lymphocyte activating factor |

TABLE 1-continued
SOLUBLE BIOLOGICAL MEDIATORS

| | |
|---|---|
| LAFTC | T-lymphocyte activating factor |
| LAP | Soluble nondialyzable factor acting on PHA-stimulated thymocytes |
| LCHA | Lymphocyte chemotactic factor |
| LFM | Leukocyte endogenous factor |
| LF | Leukotactic factor |
| LIF | Leukocyte inhibitory factor |
| LIF$_1$ | Leukocyte inhibitory factor |
| LIF$_2$ | Lymphocyte inhibitory factor |
| LMF | Lymphocyte mitogenic factor |
| LT | Lymphotoxin |
| LTF | Lymphocyte trapping factor |
| MAF | Macrophage activating factor |
| MAGF | Macrophage aggregation factor |
| MCF | Monocyte chemotactic factor |
| MCF | Macrophage cytotoxic factor |
| MDF | Macrophage disappearance factor |
| MEF | Migration enhancement factor |
| MF | Mitogenic Factor |
| MIF | Migration inhibitory factory |
| MILF | Macrophage inhibitory-like factor |
| MLF-T$_s$F | Mixed lymphocyte reaction suppressor factor |
| MLRS | Mixed lymphocyte reaction suppressor |
| NAF | Normal cell activating factor |
| NALE | Nonadherent lymphocyte suppressor acting early in leukocyte response |
| NALL | Nonadherent lymphocyte suppressor acting late in leukocyte response |
| NIF-T | Neutrophil migration inhibition factor |
| NIP | Normal immunosuppressive protein |
| NSM | Non-specific mediator (T-cell derived) |
| OAF | Osteoclast activating factor |
| PAIF | Peritoneal adherence inhibitor |
| PEF | Phagocytosis enhancing factor |
| PSF | Polymorphonuclear stimulating factor |
| SCDF | Stem cell differentiating factor |
| SIIR | Suppressor of the initiation of primary immune response |
| SIRET | Specific immune response enhancing factor |
| SIRS | Soluble immune response suppressor |
| SMAF | Specific macrophage arming factor |
| SRF | Skin reactive factor |
| SSF | Soluble suppressor factor |
| TCGF | Interleukin 2 |
| | Interleukin 3 |
| TCSDPT | T-cell suppressor depressing passive transfer (of contact sensitivity) |
| TEF | Thymus extract factor |
| TF | Transfer factor |
| TI | Tumor inhibitor (from fibroblast cultures) |
| TNF | Tumor necrosis factor |
| TRF | T-cell replacing factor |
| XRS | Xenogenic reconstruction factor |

TABLE 2
MITOGENIC AND ANTIGENIC AGENTS

Adrenalcorticotropic hormone (ACTH)
Antilymphocytic antisera (eg. OKT3)
B-cell growth factor
Colony stimulating factor (CSF)
Concanavalin A (Con A)
Corticosteroids
Cyclic adenosine monophosphate (cyclic AMP)
Epidermal growth factor (EGF)
Epinephrine
Estrogen
Fibroblast growth factor (FGF)
Glucagon
Growth hormone somatotropin (GH)
Human chorionic gonadotropin (HCG)
Insulin
Interleukin 1 (IL-1)
Interleukin 2 (IL-2)
Isoproterenol
Lentil lectin
Macrophage activation factor (MAF)
Mitogenic factor (MF)
Mixed lymphocyte reaction (MLR)

TABLE 2-continued

MITOGENIC AND ANTIGENIC AGENTS

Multiplication stimulating activity (MSA)
Nonsupressible insulin-like activity (NSILA-S)
Osteoclast activating factor (OAF)
Phytohemagglutinin (PHA)
Platelet derived growth factor (PDGF)
Serum
Sheep red blood cells
Somatomedin A
Somatomedin C
Soy bean lectin
*Staphlococcal enterotoxin* A (SEA)
*Staphlococcal enterotoxin* B (SEB)
Thyroxine (T$_4$)
Tri-iodothyronine (T$_3$)
Trypsin
Vitamin A The present invention provides a process for inducing white blood cells to produce soluble biological mediators by treating the cells with a mitogenic or antigenic agent. In accordance with the present invention, it has now been found that when red blood cells are included with the white blood cells in controlled amounts, a dramatic increase in the production of mediator is achieved in comparison to the amount produced in the absence of red blood cells.

The white blood cells can be obtained from a variety of mammals, including, for example, cows, sheep, horses, dogs, cats and other domestic animals and pets. For the production of products designed for use with human patients, human white blood cells are preferred, although not necessary. A preferred source of these cells are human buffy coats, available from Red Crosses or similar organizations throughout the world. For products designed for use with animals, white blood cells from the animal to be treated will generally be preferred.

The red blood cells also can be obtained from a variety of sources. Again, it is normally preferable to use red blood cells from the organism which is to be treated with the products produced by the induction. Thus, for products intended for use on humans, e.g. gamma interferon, both human red blood cells and white blood cells are preferred.

As discussed in detail below (see Example 6), the most convenient and therefore preferred way of obtaining the red blood cells for use with the invention is by processing human buffy coats so that a controlled amount of red blood cells (on the order of between 10 and 50 red blood cells for each white blood cell) remain commingled with the white blood cells upon the completion of the processing. Alternatively, as also discussed in detail below, a complete separation of white and red blood cells can be made and then the desired concentration of red blood cells (i.e., between 10 and 50 red blood cells per white blood cell) can be reintroduced to the population of white blood cells.

Various mitogenic and antigenic agents can be used with the present invention, such as those illustrated hereinabove. For the production of human gamma interferon, PHA-P manufactured by P/L Biochemicals (Milwaukee, Wis.) is considered the preferred mitogenic agent. With PHA-P and red blood cell to white blood cell ratios varying between 10 to 1 and 50 to 1 increases in interferon production up to 1000% have been achieved. Similar results can be achieved with other mitogenic and antigenic agents.

In general, the optimum range of red blood cell to white blood cell ratios will vary depending on such factors as the source of the cell populations, the type of mitogenic or antigenic agent employed, the processing conditions and other factors employed in the invention.

Various materials and procedures are common to the examples presented below. Accordingly, for convenience, a description of these common elements is presented here.

MATERIALS

Phosphate Buffered Saline

Phosphate buffered saline (PBS) was prepared by dissolving sodium chloride (0.14M), potassium chloride (2.7 mM), and dibasic sodium phosphate (6.5 mM) in purified water. The pH of the solution was adjusted to 7.4±0.2 with concentrated sodium hydroxide.

aγ Serum

Human aγ serum was prepared from human plasma obtained from the American Red Cross. Plasma from approximately 100 donors was pooled and stirred for three hours at room temperature in a large beaker containing glass beads. A sufficient amount of calcium chloride was added to the plasma to produce a calcium chloride concentration of 0.02M±0.005M. After the three hours of mixing, the plasma was stored for a minimum of 10 hours at 2° C. to 8° C. Thereafter, the clot was removed and the plasma centrifuged either at 4500×g for 45 minutes or at 18,000–22,000×g for 1.5 minutes at a temperature of between 2° C. and 8° C. To the supernatant (serum) was then added, with stirring, a sufficient amount of ammonium sulfate to reach about 40% saturation (at 25° C.) with respect to ammonium sulfate. The ammonium sulfate was added over a period of 2 or more hours and at a temperature of 2° C. to 8° C. The suspension was then stirred for a minimum of 10 hours at 2° C. to 8° C. and then centrifuged at approximately 4,500×g for 45 minutes or 14,000–22,000×g for 5 minutes at 2° C. to 8° C. A sufficient amount of neomycin sulfate (GIBCO, Grand Island, N.Y. was then added to the supernatant to produce a concentration of 25 μg/ml. The resulting solution was then diafiltered at 2° C. to 8° C. with about 7 volumes of sterile PBS in a hollow fiber cartridge having a molecular weight cut-off of about 5,000–10,000 daltons. Finally, the serum was filtered through a non-fiber releasing 0.22μ Millipore filter. Prior to use the serum was heated to 56° C. and held at that temperature for one hour to inactivate some complement components present in the serum.

Modified L-RPMI 1640 Medium

Modified L-RPMI 1640 medium was prepared by adding to 520 grams of L-RPMI 1640 (GIBCO, Grand Island, N.Y. the following ingredients: 100 grams sodium bicarbonate; 120 grams neomycin added as neomycin sulfate (GIBCO, Grand Island, N.Y.) 297.88 grams of HEPES buffer; 14.6 grams of L-glutamine (SIGMA Chemical Co., St. Louis, Mo.); and a sufficient amount of purified water to produce a final volume of 50 liters. The medium was prepared by dissolving the RPMI, by stirring, in a volume of purified water corresponding to about 90% of the final volume of the medium. Thereafter, the sodium bicarbonate, neomycin, HEPES buffer and the L-glutamine were added with continued stirring. After all the ingredients were dissolved, the pH of the mixture was adjusted to a value between 6.9 and 7.0 by adding concentrated sodium hydroxide or hydrochloric acid, as appropriate. Finally, the medium was filtered through a non-fiber releasing 0.22μ Millipore filter.

PROCEDURES

Preparation of White Blood Cells By The Ficoll-Hypaque Gradient Method

Human white blood cell populations were prepared by the Ficoll-Hypaque gradient method as follows.

First, buffy coat cell suspensions obtained from the American Red Cross were pooled. At least 120 buffy coats were used for each pool and the buffy coats were not segregated by blood type. Next, approximately 20 ml of buffy coat suspension was added to 25 ml of Ficoll-Hypaque gradient in a 50 ml conical sterile centrifuge tube.

The cell and Ficoll-Hypaque suspension was centrifuged at room temperature at 1200 RPM in a DPR 6000 centrifuge for 30 minutes. The plasma above the interface was discarded. The cells at the interface, constituting the mononuclear cell fraction, were collected at the interface and just below the interface. This cell suspension was mixed with three volumes of phosphate buffered saline (at 4° C.) and centrifuged again at 1200 RPM in the same centrifuge for 10 minutes to pellet the cells.

The pelleted cells were resuspended in the modified L-RPMI 1640 medium, described above, to which had been added approximately 1–5% of aγ serum (described above) to produce a protein concentration of approximately 1.25 mg/ml of solution. The final concentration of cells was adjusted to be approximately $1-2 \times 10^7$ cells per ml.

Preparation Of White Blood Cells By Ammonium Chloride Lysis

Human white blood cell populations were prepared by the ammonium chloride lysis technique as follows.

First, buffy coat cell suspensions obtained from the American Red Cross were pooled and then placed into 50 ml sterile conical centrifuge tubes. Each pool included at least 120 buffy coats which were not segregated by blood type. The cells were centrifuged at 4° C. at 1000 RPM in a DPR 6000 centrifuge. The plasma layer (approximately 10 ml) was discarded. The surface white blood cell layer, comprising about 10–15 ml and including many red blood cells, was collected into a separate tube and labelled the "white blood cell fraction". The red blood cells remaining in the tube were labelled the "red blood cell fraction" and kept for further processing (see discussion below entitled "Preparation of Red Blood Cells").

The white blood cell fraction was combined with 2–3 volumes of phosphate buffered ammonium chloride solution (pH 7.4) and mixed for 15 minutes at 4° C. The lysed red blood cell/white blood cell mixture was then centrifuged to pellet the cells. The supernatant containing the hemoglobin was discarded. The cell pellet was then mixed with approximately 40 ml of the ammonium chloride solution and again mixed for 15 minutes at 4° C. Thereafter, the cell pellet was collected by centrifugation under the conditions described above, the supernatant discarded, the cells washed once with 40 ml of cold phosphate buffered saline, recentrifuged, and finally resuspended in the modified L-RPMI 1640 medium, described above, to which had been added approximately 1–5% of aγ serum (described above) to produce a protein concentration of 1.25 mg/ml of solution. The final concentration of cells was adjusted to be approximately $1-2 \times 10^7$ cells per ml.

Preparation Of Red Blood Cells

Human red blood cells were prepared by washing the "red blood cell fraction" obtained during the preparation of white blood cells by the ammonium chloride lysis method, supra, with phosphate buffered saline. The red blood cell fraction was mixed vigorously with 1–2 volumes of phosphate buffered saline at 4° C. The cells were pelleted at 1000 RPM at 4° C., the aqueous supernatant was discarded and the top 10% of the red blood cell layer was also discarded. The washing process was repeated again twice (a total of three washes) with the final cell pellet being suspended in the modified L-RPMI 1640 medium described above to produce a final cell density of $1 \times 10^9$ red blood cells per ml. By means of this process, there was less than 1 white blood cell per million red blood cells detectable.

Preparation Of Red Blood Cell Fractions

Red blood cell fractions including and not including cell membranes were prepared as follows. First, red blood cells were prepared as described above except that the cells were not resuspended after the final wash in modified L-RPMI 1640 medium, but rather in sterile distilled water at 4° C. Hemolysis was carried out at 4° C. until visual inspection of the red blood cell lysate showed no intact red cells.

The mixture was centrifuged at 20,000 RPM in a Beckman J2-21 centrifuge using a Beckman JA-20 rotor at 4° C. for 30 minutes. The supernatant ("fraction not including cell membranes") was separated from the pellet. The pellet was washed consecutively 2 times with phosphate buffered saline at 4° C. and the final resuspension was in modified L-RPMI 1640 medium ("fraction including cell membranes"). The fraction not including cell membranes was adjusted with concentrated modified L-RPMI 1640 medium to a final concentration of 1×modified L-RPMI 1640 medium. All concentrations were adjusted to be equivalents of the whole red blood cell preparation, supra, for the same cell density ($1 \times 10^9$ cells per ml) so that the addition of equal volumes of either the fraction including cell membranes or the fraction not including cell membranes was equivalent to the addition of an equal volume of the whole red blood cell preparation, in that the contents of each volume was attributable to the same number of red blood cells.

The examples which follow illustrate the various aspects of the invention. It is to be understood that the examples are not to be construed as limiting the scope of the invention in any manner.

EXAMPLE 1

This example demonstrates the effect of red blood cells on the production of HuIFN-γ by white blood cells. It also demonstrates the effects of red blood cell fractions which include and do not include cell membranes on that production. The results are shown in FIGS. 1 and 2.

The data in these figures were obtained using the materials and procedures described above. All cells were incubated at 37° C., 5% $CO_2$ and 95% humidity for four days in modified L-RPMI 1640 medium to which was added approximately 1%–5% human aγ serum to produce a final protein content of approximately 1.25 mg/ml of solution. After the four day incubation, the cells were removed from the medium by centrifugation at 1,000 RPM in a DPR 6000 for ten minutes at 4° C. The supernatant was removed, sterile filtered through an 0.22 micron filter and titered for interferon activity (using HEp-2 cells and VSV virus). An in-house gamma interferon standard served as the reference standard. All inductions were with optimal concentrations of PHA-P (P/L Biochemicals, Milwaukee, Wis.) which varied from lot to lot, but was in the range of 5-10 micrograms of PHA-P per ml of induction. The cells were incubated under stationary conditions at a density of $1 \times 10^6$ cells per $cm^2$ in an area of 150 $cm^2$ in a tissue culture petri dish (FIG. 1) or an area of 2 cm2 in a 24 well tissue culture plate (FIG. 2). In FIG. 1, one hundred milliliters of media were used per plate; in FIG. 2, two milliliters of media were used in each well. As discussed above, for each of these experiments, the red blood cells and white blood cells came from a mixture of buffy coats. The buffy coats were not separated by blood types and the pool included a minimum of 120 buffy coats.

Figure 1:
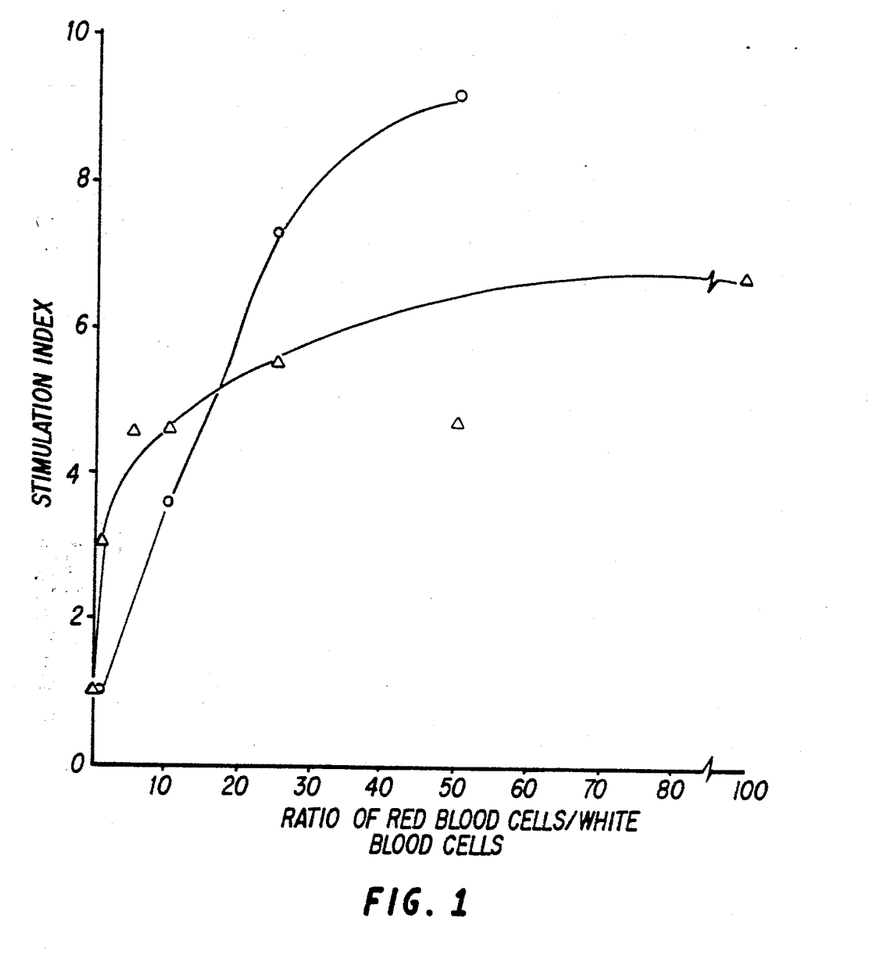
FIG. 1 shows the effects of various ratios of red blood cell to white blood cells on gamma interferon production by white cell populations obtained by the Ficoll-Hypaque gradient method (circles) and the ammonium chloride lysis technique (triangles).
Figure 2A:
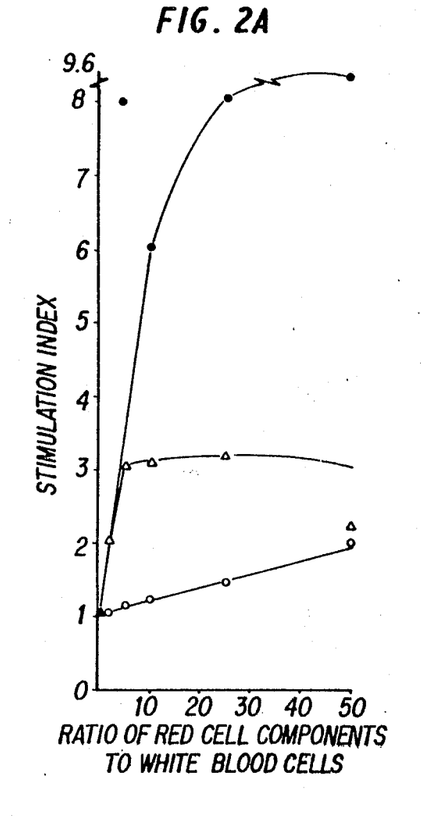
FIG. 2 shows the effects of whole red blood cells (closed circles), a whole red blood cell fraction which includes cell membranes (open triangles) and a whole red blood cell fraction which does not include cell membranes (open circles) on the production of gamma interferon by populations of white blood cells prepared by the Ficoll-Hypaque gradient method (panel A) and the ammonium chloride lysis technique (panel B).
Figure 2B:
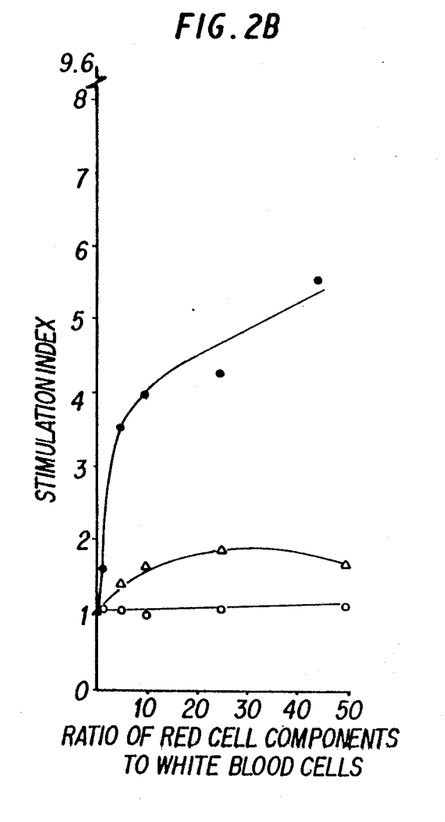

FIG. 1 shows the dramatic increase in gamma interferon production as a result of adding red blood cells to white blood cell populations. The circles represent white blood cells prepared by the Ficoll-Hypaque centrifugation technique described above. The triangles represent white blood cells prepared by the ammonium chloride lysis technique, also described above. For both curves, the red blood cells were prepared in the manner described under the heading "Preparation of Red Blood Cells". The results are given in terms of the "stimulation index", which was defined as the ratio of the titer of HuIFN-γ at a particular red blood cell to white blood cell ratio (RBC/WBC) to the titer for pure white blood cells with no red blood cells present.

Both curves in FIG. 1 show very large increases in gamma interferon production in the presence of red blood cells. For the Ficoll-Hypaque separated cells, stimulation indexes on the order of 3 to 10 are produced by RBC/WBC ratios varying from about 10 to 1 to about 50 to 1. For the ammonium chloride treated cells, the indexes range from 4 to 6 for the same range of RBC concentrations. In terms of HuIFN-γ production, these results show that on the order of a 1000% increase in production can be obtained for RBC/WBC ratios between 10 to 1 and 50 to 1.

FIG. 2 shows the effects on HuIFN-γ production of whole red blood cells (closed circles), the red blood cell fraction including cell membranes described above (open triangles) and the red blood cell fraction not including cell membranes, also described above (open circles). The figure is divided into panels A and B. Panel A represents cells prepared by the Ficoll-Hypaque density centrifugation method; panel B represents cells prepared by the ammonium chloride lysis technique. The numbers on the horizontal axis represent, for the closed circle data points, the ratio of red blood cells to white blood cells and for the open circle and open triangle data points, the ratio of the number of red blood cells whose content corresponds to the content of the red blood cell fraction added, to white blood cells. The vertical axis is again given in terms of the "stimulation index" defined above.

As shown in FIG. 2, whole red blood cells and a red blood cell fraction including cell membranes both are capable of stimulating HuIFN-γ production by white blood cells, with the whole red blood cells being most effective. The red blood cell fraction not including cell membranes, on the other hand, has a very limited stimulatory effect.

EXAMPLE 2

This example illustrates the effects of different mitogens on the production of HuIFN-γ by white blood cells in the presence of red blood cells. The results are shown in Table 3. The data was obtained by incubating $2 \times 10^6$ white blood cells in 2 ml of modified L-RPMI 1640 medium to which had been added 1.0% human aγ serum. The induction was carried out under stationary conditions for 4 days at 37° C., 5% $CO_2$ and 95% humidity. Each inducer was used at a predetermined optimal concentration for that inducer (e.g., PHA-P, 10 μg/ml; OKT3, 10 ng/ml). The RBC/WBC ratio for these runs was between 10 to 1 and 20 to 1.

TABLE 3

| INDUCTION OF GAMMA IFN BY DIFFERENT MITOGENS | |
|---|---|
| Inducer | Gamma IFN Titer relative to PHA-P |
| Phytohemagglutinin and sources: | |
| a. P/L Biochemicals (PHA-P) | 1.00 |
| b. Calbiochem (PHA-M) | 0.25 |
| c. P/L Biochemicals (PHA-M) | 0.03 |
| d. Sigma (PHA-V) | 0.63 |
| e. Burrough's Welcome (PHA) | 0.17 |
| f. Miles Laboratories (PHA-L) | <0.03 |
| g. P/L Biochemicals (PHA-L) | <0.03 |
| Concanavalin A | 0.32 |
| *Staphlococcal enterotoxin* A | 1.03 |
| *Staphlococcal enterotoxin* B | 0.50 |
| Lentil lectin | 0.16 |
| OKT3 monoclonal antibody | 0.46 |
| Soybean lectin | 0.29 |

As shown in Table 3, PHA-P (P/L Biochemicals, Milwaukee, Wis.) and staphlococcal enterotoxin A (Microbial Biochemistry Branch, Public Health Service, Department of HEW, Cincinnati, OH. were most effective in inducing production of HuIFN- γ. Next in line were PHA-V (Sigma Chemical Co., St. Louis, Mo.), staphlococcal enterotoxin B (Sigma Chemical Co., St. Louis, Mo.) and OKT3 monoclonal antibody (Ortho Pharmaceuticals, Inc., Raritan, NJ). PHA-M produced by Calbiochem-Behring Corporation (San Diego, CA), PHA produced by Burroughs Welcome Company (Greenville, NC), concanavalin A produced by Calbiochem-Behring Corporation and lentil and soybean lectin (Dept. of Biol. Research, Rutgers University, NJ) each had less than 50% the inductive effect of PHA-P, while PHA-M (P/L Biochemicals) and PHA-L (Miles Laboratories, Elkhart, Ind., or P/L Biochemical) had little effect in comparison to PHA-P. In terms of large scale human gamma interferon production, PHA-P is considered the preferred mitogen.

EXAMPLE 3

This example shows the effects of red blood cells from different sources on the production of gamma interferon by human white blood cells. The experiments were done under the incubation conditions described in Example 2. The red blood cell to white blood cell ratio in all four experiments was constant at 15 red blood cells per white blood cell. The white blood cells were prepared by the ammonium chloride method described above and used at a concentration of $1 \times 10^6$ cells per $cm^2$ in a 24 well plate where each well had a surface area of 2 square centimeters. Two milliliters of modified L-RPMI 1640 medium with 1% human aγ serum was used in each well. The inducer was PHA-P at a concentration of 5 micrograms per ml. The results are shown in Table 4.

TABLE 4

HETEROLOGOUS SPECIES RBC STIMULATION

| Red Blood Cell Source | Stimulation Index |
| --- | --- |
| None | 1.0 |
| Human, mixed population | 5.0 |
| Chicken | 1.0 |
| Rabbit | 1.6 |
| Sheep | 5.9 |

As shown in this Table, the stimulation of the white blood cells to produce gamma interferon is dependent on the source of red blood cells. In two of the heterologous cases, chicken and rabbit, there was minimal or no stimulation above what was observed with unstimulated white blood cells, i.e., white blood cells with no red blood cells added. However, the addition of a mixed population of human red blood cells (types A, B, AB and O) gave a five-fold stimulation and the addition of sheep red blood cells gave almost a six-fold stimulation above unstimulated cells.

Although not wishing to be bound by any particular theory of operation, these results suggest that there may be an antigenic stimulation of gamma interferon in the presence of PHA caused by 1) cross matched human red blood cells, i.e. A type blood going into a B type person; or 2) sheep red blood cells. Sheep red blood cells may have this effect because of their agglutination or clumping effect on T lymphocytes. See T. W. Chang, et al., "Cellular Origin and Interactions Involved in γ-Interferon Production Induced by OKT3 Monoclonal Antibody", Journal of Immunology, Vol. 128, February 1982, pages 585–589. Hence the differences in stimulation of gamma interferon shown in Table 4 for different sources of red blood cells may be due to (1) antigenic stimulation by a mixed population of red and white blood cells and (2) the recognition by white blood cells of a sheep red blood cell antigen.

EXAMPLE 4

This example considers the effect on the induction of gamma interferon of segregating the white and red blood cells into A, B, AB and O blood types. The experiments were done by taking individual buffy coats and typing them by blood type. The individual buffy coats were then pooled by blood type. There was no less than 3 individual buffy coats in each pool. White blood cells were then prepared by the ammonium chloride lysis method described above and red blood cells were prepared as described in the section entitled "Preparation of Red Blood Cells". The "mixed" cell populations were prepared by mixing equal parts of A, B, AB and O red cells or a, b, ab and o white blood cells. The cells were incubated under the conditions of Example 3 except that the RBC/WBC ratio was 10 to 1 rather than 15 to 1. The results are shown in Table 5.

TABLE 5

DEPENDENCE OF GAMMA INTERFERON PRODUCTION ON WBC AND RBC SOURCES

| | Stimulation Index | | | | |
| --- | --- | --- | --- | --- | --- |
| | White blood cell source | | | | |
| | o | a | b | ab | Mixed |
| RBC Source - mixed A, B, AB and O Cells | 10 | 5 | 5 | 6.7 | 6.7 |
| | Red blood cell source | | | | |
| | O | A | B | AB | Mixed |
| WBC Source - mixed a, b, ab and o Cells | 10 | 10 | 10 | 10 | 6.7 |

As shown in this Table, there is a substantial stimulation of interferon production for each of the cell type combinations tested. The data for the various red blood cell types shows that the various types of red blood cells each stimulate a mixture of white blood cells to essentially the same extent. The data for the various white blood cell types shows that the source of white blood cells has some effect on interferon production in that white blood cells isolated from type A or B buffy coats, as well as to some extent those isolated from type AB buffy coats, are somewhat less subject to stimulation than those isolated from type 0 buffy coats. Although not wishing to be bound by any particular theory of operation, it is believed that this may be due to the recognition of the A and B red blood cell antigens by the type o white blood cells causing antigenic stimulation of those cells. In general, Table 5 further reinforces the strong stimulatory effect of red blood cells on white blood cells in the production of human interferon, irrespective of the particular type of red or white blood cells.

EXAMPLE 5

This example compares stationary versus spinning culture conditions with regard to the induction of HuIFN-γ in white blood cells. The inductions were done in modified L-RPMI 1640 medium containing 1% human aγ serum. Five micrograms per ml of PHA-P was added to the medium and the cells were incubated for 4 days at 37° C. The white blood cell density was $1 \times 10^6$/ml and the RBC/WBC ratio was 10 to 1.

Tissue culture petri dishes (150 cm$^2$) were used for the stationary tests. Spinner flasks containing a spinning bar to keep the cells suspended were used for the spinning tests. Under stationary conditions, the cells form a layer on the bottom surface of the petri dish with the liquid medium above the cells. The cell density for this condition is high, but the volume of medium is low (100 ml) because of the size of the container. For comparison, the volumes of the spinner containers were either 250 or 500 ml.

Incubations for both the stationary and spinning conditions were performed in a $CO_2$ incubator set for 5% $CO_2$ and 95% humidity at 37° C. Spinning tests were also performed in airtight bottles in a water bath at 37° C. For these tests, the medium was modified to contain 50 mM sodium bicarbonate (twice the concentration present in the standard modified L-RPMI 1640 medium, described above).

The results of the comparison tests are shown in Table 6.

TABLE 6

COMPARISON OF INDUCTION CONDITIONS

| $CO_2$ Source* | Culture Conditions | Volume (mls) | Interferon Yield per $10^6$ WBC (units $\times 10^3$) |
|---|---|---|---|
| A | Stationary | 100 | 3.32 |
| A | Spinning | 250 | 0.45 |
| A | Spinning | 500 | 0.83 |
| A | Spinning | 500 | 1.31 |
| B | Spinning | 250 | 1.12 |
| B | Spinning | 500 | 0.82 |

*A = 5% $CO_2$ + 95% humidity in a $CO_2$ incubator.
B = 50 mM $NaHCO_3$ in an airtight vessel.

As shown in this Table, stationary conditions are plainly superior to spinning conditions. Whether the spinning culture is done in a water bath or a $CO_2$ incubator, spinning results in less efficient gamma interferon production compared to stationary growth by a factor varying between 2.5 and 7-fold.

EXAMPLE 6

This example relates to the large scale production of a mixture of white blood cells and a controlled amount of red blood cells. In particular, the example relates to an easy-to-use method for obtaining the desired mixture.

The method employs buffy coats obtained from the American Red Cross. Buffy coats from several human donors were pooled into a sterile 500 ml measuring cylinder. The pooled buffy coats were then distributed into sterile 50 ml centrifuge tubes and centrifuged at $1000 \times g$ for 10 minutes at 4° C. The plasma and platelets were aspirated from each tube and the white cell layers containing some red blood cells were removed. The white cell layers from two centrifuge tubes were combined in a 50 ml centrifuge tube to which was added sufficient phosphate buffered saline to bring the final volume to 50 ml. Calcium chloride and magnesium chloride at concentrations of 1–2 mM and 0.8–1.6 mM, respectively, were added to the phosphate buffered saline used to dilute the white cell layers.

The diluted white cell layers were again centrifuged at $1000 \times g$ for 10 minutes at 4° C. Thereafter, the plasma and platelets were aspirated and the new white cell layer was removed. This layer was suspended in modified L-RPMI 1640 medium and then used in the induction of soluble biological mediators, including gamma interferon, by mitogenic and antigenic agents. Alternatively, the new white cell layer can be washed with cold sterile phosphate buffered saline and centrifuged at $800-1000 \times g$ for 10 minutes prior to suspension in modified L-RPMI medium.

Analysis of the RBC/WBC ratios obtained by following the above procedure has shown that the method reliably results in ratios between 10 to 1 and 50 to 1, which is precisely the range in which the enhanced induction is observed (see Example 1). Table 7 presents typical data "before" and "after" application of the process to human buffy coats obtained from the American Red Cross.

TABLE 7

| RBC to WBC Ratio | |
|---|---|
| Before | 1000:1 |
| After | 10–50:1 |

| WBC Population | | |
|---|---|---|
| | Granulocytes | Mononuclear cells |
| Before | 68% | 32% |
| After | 55% | 45% |

Although specific embodiments of the invention have been described and illustrated, it is to be understood that modifications can be made without departing from the invention's spirit and scope. Thus, although the invention has been illustrated with reference to white blood cells obtained from humans, it is equally applicable to white blood cells obtained from other mammals. Similarly, although the product gamma interferon has been used to illustrate the invention, the invention can be practiced to produce other soluble biological mediators.

What is claimed is:

1. In a process for producing gamma interferon from white blood cells wherein the gamma interferon is produced by inducing the white blood cells with a mitogenic or antigenic agent and collecting the gamma interferon generated by the induced cells, the improvement comprising inducing the white blood cells in the presence of an effective amount of red blood cells or a red blood cell fraction which comprises cell membranes so as to enhance the induction of gamma interferon by the mitogenic or antigenic agent by a factor of about two or more in comparison with the amount of gamma interferon produced in the absence of red blood cells.

2. The process of claim 1 wherein phytohemagglutinin is the mitogenic agent.

3. The process of claim 1 wherein the red blood cells are present in an amount such that the ratio of red to white blood cells is between about 10 to 1 and about 50 to 1.

4. In a process for producing messenger RNA for gamma interferon wherein the messenger RNA is produced by inducing white blood cells with a mitogenic or antigenic agent, the improvement comprising inducing the white blood cells in the presence of an effective amount of red blood cells or a red blood cell fraction which comprises cell membranes so as to enchance the inductive effect of the mitogenic or antigenic agent on the white blood cells by a factor of about two or more in comparison with the inductive effect in the absence of red blood cells.

5. The process of claim 4 wherein phytohemagglutinin is the mitogenic agent.

6. The process of claim 4 wherein the red blood cells are present in an amount such that the ratio of red to white blood cells is between about 10 to 1 and about 50 to 1.

7. The process of claim 1 wherein the presence of the red blood cells is achieved by centrifuging a buffy coat which contains white and red blood cells, removing a first white cell layer which contains some red blood cells from the centrifuged product so formed, diluting said first white cell layer with a liquid compatible with both white and red blood cells, centrifuging the diluted first white cell layer and removing a second white cell layer containing some red blood cells from the centrifuged product so formed.

8. The process of claim 4 wherein the presence of red blood cells is achieved by centrifuging a buffy coat which contains white and red blood cells, removing a first white cell layer which contains some red blood cells from the centrifuged product so formed, diluting said first white cell layer with a liquid compatible with both white and red blood cells, centrifuging the diluted first white cell layer and removing a second white cell layer containing some red blood cells from the centrifuged product so formed.

* * * * *

UNITED STATES PATENT AND TRADEMARK OFFICE
CERTIFICATE OF CORRECTION

PATENT NO. : 4,591,557
DATED : May 27, 1986
INVENTOR(S) : Lynne D. Keyes and Douglas Testa It is certified that error appears in the above-identified patent and that said Letters Patent is hereby corrected as shown below:

Abstract/line 10 insert --about-- before "10 to 1"

Column 1/line 11 "it" should read --It--

Column 1/line 27 "Inteferon" should read --Interferon--

Column 1/line 33 "Ieukocyte" should read --leukocyte--

Column 1/line 41 insert --.-- after "methods"

Column 6/line 17 insert --.-- after "water"

Column 9/line 13 "1 X $^{106}$" should read --1 X $10^6$--

Signed and Sealed this

Twenty-eighth Day of April, 1987

Attest:

DONALD J. QUIGG

Attesting Officer     Commissioner of Patents and Trademarks